(12) United States Patent
Eizen et al.

(10) Patent No.: US 9,468,596 B2
(45) Date of Patent: Oct. 18, 2016

(54) MULTI USE COSMETIC FORMULA

(71) Applicants: Micha Eizen, Lake Forest, CA (US);
Dina Soker, Lake Forest, CA (US)

(72) Inventors: Micha Eizen, Lake Forest, CA (US);
Dina Soker, Lake Forest, CA (US)

( * ) Notice: Subject to any disclaimer, the term of this patent is extended or adjusted under 35 U.S.C. 154(b) by 0 days.

(21) Appl. No.: 14/630,485

(22) Filed: Feb. 24, 2015

(65) Prior Publication Data
US 2015/0238409 A1    Aug. 27, 2015

Related U.S. Application Data

(60) Provisional application No. 61/944,073, filed on Feb. 25, 2014.

(51) Int. Cl.
| | | |
|---|---|---|
| *A61K 8/02* | (2006.01) | |
| *A61K 8/92* | (2006.01) | |
| *A61K 8/19* | (2006.01) | |
| *A61K 8/73* | (2006.01) | |
| *A61Q 19/00* | (2006.01) | |
| *A61Q 15/00* | (2006.01) | |

(52) U.S. Cl.
CPC ............... *A61K 8/922* (2013.01); *A61K 8/19* (2013.01); *A61K 8/73* (2013.01); *A61K 8/737* (2013.01); *A61Q 15/00* (2013.01); *A61Q 19/00* (2013.01); *A61Q 19/007* (2013.01)

(58) Field of Classification Search
None
See application file for complete search history.

(56) References Cited

U.S. PATENT DOCUMENTS

2012/0034320 A1 * 2/2012 Murray ............... A61K 31/375
424/678

* cited by examiner

*Primary Examiner* — Susan Tran
(74) *Attorney, Agent, or Firm* — Randolph Bretton; The Law Office of Randolph Bretton

(57) ABSTRACT

The invention relates to formulations that comprise non-irritating non-toxic compounds that may be applied to the skin for generally improvement of health and beauty. The formulations include core ingredients of minerals, oils, and emulsifiers. Additional ingredients may be added to provide a variety of formulations for skin hydration, softening, soothing, deodorizing, and cosmetic application. The formulations may be use as a carrier for cosmetics, fragrances, or therapeutic agents.

16 Claims, No Drawings

MULTI USE COSMETIC FORMULA

CROSS REFERENCE TO RELATED APPLICATIONS

This application claims priority to provisional application 61/944,073, filed Feb. 25, 2014, which is hereby incorporated by reference in its entirety.

FIELD OF THE INVENTION

The invention relates to a non-irritating non-toxic formulation that may be applied to the skin. The compositions may provide hydration, softening, soothing, and/or may provide a carrier for cosmetics, fragrances, or therapeutic agents.

BACKGROUND

Many modern body care products contain chemicals that have been identified as irritants or toxins. Even if only present in small amounts, the cumulative effect of continued exposure to irritants or toxins is thought to be detrimental over a period of time. Some toxins such as propylene glycol and aluminum have been linked to diseases like cancer and Alzheimer. The Inventors have formulated a multiuse cosmetic formulation to provide consumers with skin care products which do not contain skin irritants, toxins or preservatives but still provide the desired cosmetic results.

SUMMARY OF THE INVENTION

The multi-use cosmetic formula contains ingredients which are generally recognized as safe (GRAS) naturally accruing minerals and ingredients, formulated to provide a cosmetically safe and beneficial solution and when applied to the skin will improve appearance, feel, smell, color and texture. The multi-use cosmetic formula does not contain ingredients that are known or suspected to be irritants or toxins.

The multi-use cosmetic formula can be used as a hydrating formula or in a variety of applications, including but not limited to a soothing lotion, skin softener and/or skin lubricating product. It may also be combined with other non-irritating no-toxic compounds for additional applications. By way of non-limiting examples, it may be combined with non-irritating or no-toxic pigments to provide a cosmetic formulation, or non-irritating no-toxic anti-bacterial ingredients and/or fragrances to provide a deodorant formulation. The multi-use cosmetic formula may be combined with non-irritating non-toxic oils to provide a formulation useful for damaged skin.

DETAILED DESCRIPTION OF THE INVENTION

The multi-use cosmetic formula is an aqueous formula containing only non-irritating non-toxic ingredients. Common to all embodiments of the multi-use cosmetic formula are the core minerals, oils, and emulsifiers. Although the amounts and proportions of these core ingredients are subject to some variation, the core ingredients are common to the various embodiments of the multi-use cosmetic formulations. The various multi-use cosmetic formulations may contain compounds, in addition to the core ingredients, provided they are non-irritating and non-toxic. By way of example, natural oils may be added to provide a soothing effect to the formulation when applied to normal or damaged skin, or, natural fragrant extracts including essential oils may be added to comprise a perfume of deodorant formula. Natural pigments may be added to provide color, for a masking, makeup, or sun blocking application for cosmetic uses.

The core multi-use cosmetic formula, is comprised of the following compounds and percentages as specified in Table 1, dissolved in water, preferably purified or distilled water. All percentages are according to mass, added to an amount of water necessary to equal 100 percent. This applies to all formulas disclosed herein. By way of example, a formulation containing 10 percent compound X may be prepared by dissolving 10 grams of compound X in 90 grams of water. A formulation containing 10 percent compound X and 5 percent compound Y, may be prepared by dissolving 10 grams of compound X and 5 grams of compound Y in 85 grams of water. In Table 1, where the total weight of compounds varies, the total amount of water will vary inversely to the weight of the compounds, to comprise the remaining 100 percent.

TABLE 1

Core ingredients: Percentage by weight dissolved in in water.

| Water | |
|---|---|
| Water, preferable purified or distilled | As necessary to equal 100% |
| Minerals | |
| Magnesium compounds (Sulfates, Phosphates, Chlorides, Oxides, citrates, carbonates, Glycinate, Taurate, Theonate, salts) | about 0.001% to about 20% |
| Calcium compounds:(Carbonates, Chlorides, oxides, salts, phosphates, mono calcium phosphate) | about 0.002% to about 9%; |
| Potassium compounds: (Phosphates, Chlorides, salt) | about 0.001% to about 6% |
| Oils: One or more of the following | |
| Jojoba oil | about 0.005% to about 6% |
| Grape Seed Oil | about 0.005% to about 5% |
| Rose Hip Oil | about 0.005% to about 5% |
| Emulsifiers: One or more of the following | |
| Agar Agar | about 0.005% to about 0.4% |
| Xanthan gum | about 0.005% to about 0.4% |
| Acacia | about 0.004% to about 0.4% |

Importantly, neither the core formula nor any of the additional embodiments or formulations include irritants or toxins. Non-limiting examples of irritants and toxics are disclosed in Table 2.

Table 2 represents non-limiting examples of skin irritants or toxics which are excluded from all formulations of the invention.

TABLE 2

Examples of skin irritants or toxics which are excluded from all formulations of the invention.

| Compound |
|---|
| Aluminum compounds |
| Propylene Glycol |
| Butylene Glycol |

TABLE 2-continued

Examples of skin irritants or toxics which are excluded from all formulations of the invention.

| Compound |
|---|
| Sodium bicarbonate |
| Benzoyl peroxide |
| monoethanolamine, diethanolamine, and triethanolamine (DEA/TEA/MEA) |
| Ethoxylated surfactants and 1,4-dioxane |
| Formaldehyde |
| Synthetic Fragrances |
| Mineral oils, petroleum |
| Oxybenzone |
| Parabens |
| Phthalates |
| Polyethylene glycol (PEG) |
| Silicone-derived emollients |
| Sodium lauryl (ether) sulfate (SLS, SLES) |
| Talc |
| Triclosan |
| Potassium Alum |
| Ammonium Alum |
| butylated hydroxyanisole (BHA) |
| Boric acid and Sodium borate |
| Alcohols, including Ethanol |
| Siloxanes |

In addition, although not essential to comprise the core formula, the ingredients in Tables 3-5 are represent non-limiting examples of natural ingredients that may be beneficial when added to the core composition to comprise additional formulations. Any number of natural waxes may also be added including but not limited to Candelilla Wax, soybean wax, and floral waxes.

TABLE 3

Natural non-irritating non-toxic compounds.

| Compound | Percentage by weight |
|---|---|
| Sodium compounds: (Salts, chlorides, carbonate) | up to about 6% |
| Dead Sea salts, Salt Lake salts, Sea salts, Himalayan salts; | up to about 25% |
| Zinc compounds (Oxides, Chlorides, Gluconate, Citrate, salts) | up to about 10% |
| Silica dioxide 5.-15 micron | up to about 15% |
| Apple cider vinegar | up to about 3% |
| Emulsifiers combination; (Agar, Gellan gum, Locust bean gum, Methylcellulose, Xanthan Gum, Psyllium) | up to about 2% |
| Aloe Vera juice | up to about 6% |
| Witch Hazel extract; | up to about 4.5% |
| Sulfur compounds (MSM etc); | up to about 4% |
| Vitamin C: | up to about 0.01% |
| Vitamin B 12: | up to about 0.01% |
| Vitamin E: | up to about 0.5% |
| Omega 3, 6, 7, or 9 oil | up to about 0.5% |
| Menthol | up to about 0.008% |
| Candelilla Wax | about 10% to about 20% |
| soybean wax | about 10% to about 20% |
| floral waxes | about 8% to 15% |
| Arrow root powder | about 5% to about 10% |
| Beef tallow | about 5% to about 25% |

TABLE 4

Natural non-irritating non-toxic emulsifiers.

| Compound | Percentage by weight |
|---|---|
| Algae | about 0.004% to about 1.5% |
| Xanthan gum | about 0.004% to about 1.5% |

TABLE 4-continued

Natural non-irritating non-toxic emulsifiers.

| Compound | Percentage by weight |
|---|---|
| Cellulose | about 0.004% to about 1.5% |
| Lecithin | about 0.004% to about 1.5% |
| Guar gum | about 0.004% to about 1.5% |
| Agar agar | about 0.004% to about 1.5% |
| Pectin fruit | about 0.004% to about 1.5% |
| Gellan gum | about 0.004% to about 1.5% |
| Locust bean gum | about 0.004% to about 1.5% |
| Psyllium | about 0.004% to about 1.5% |

TABLE 5

Natural non-irritating non-toxic oils.

| Compound | Percentage by weight |
|---|---|
| Aloe Vera juice | about 0.002% to about 6% |
| Apricot kernel oil | about 0.002% to about 6% |
| Avocado oil | about 0.002% to about 6% |
| Calendula oil | about 0.002% to about 6% |
| Coconut oil | about 0.002% to about 10% |
| Evening primrose oil | about 0.002% to about 6% |
| Grape seed oil | about 0.002% to about 6% |
| Hazelnut oil | about 0.002% to about 6% |
| Jojoba oil | about 0.002% to about 6% |
| Macadamia oil | about 0.002% to about 6% |
| Rosehip oil | about 0.002% to about 6% |
| Sesame oil | about 0.002% to about 6% |
| Walnut oil | about 0.002% to about 6% |
| Wheat germ oil | about 0.002% to about 6% |
| Olive oil | about 0.002% to about 6% |
| Pumpkin seed oil | about 0.002% to about 6% |
| Safflower oil | about 0.002% to about 6% |
| Sunflower oil | about 0.002% to about 6% |
| cocoa butter, | about 8% to about 15% |
| palm oil | about 8% to about 15% |

When used as deodorant, the formula may also provide anti-bacterial benefits which prevent and inhibit the bacteria from growing in flashy folds of the body and which cause odor to develop. Magnesium, potassium and zinc salts as well as essential oils like Tea Tree, Cinnamon, clove, menthol and camphor oils may also provide antibacterial benefits when used in the formulation.

When used as soothing lotion, the formula contains oils, minerals and ingredients which are calming the skin, by way of example Vitamin E (germ wheat oil) and Zinc compounds are examples of ingredients that may provide these benefits.

When used as a moisturizing, lubricating lotion, the formula contains hydrating ingredients, vitamins, minerals which help the skin to retain moisture thus helping the skin to be less dry and hard, Magnesium chloride, jojoba oil, coconut oil, silica and sulfur (MSM) are exemplary minerals and oils for this purpose.

Table 6 discloses a non-limiting formulation that may be used as a deodorant formulation.

TABLE 6 deodorant formulation.

| Compound | Percentage by weight |
|---|---|
| Water: preferably purified or distilled | 46% |
| Magnesium Glycinate | 10% |
| Calcium Carbonate | 3% |
| Potassium Chloride | 1% |
| Sodium Carbonate: | 1.7% |

TABLE 6-continued deodorant formulation.

| Compound | Percentage by weight |
|---|---|
| Salts: (Dead Sea salts 7.5%, Sea salt 0.5%, Himalayan salt 0.3%) | 8.3% |
| Zinc oxide | 2.3% |
| Jojoba oil | 2.5% |
| Grape seed oil | 1.7% |
| Rose hip oil | 1.2% |
| Silica dioxide spheres 5-15 micron | 9.4% |
| Apple cider vinegar | 1.5% |
| Emulsifiers combination: (Agar 0.4%, Xanthan gum 0.4%, Acacia 0.4%) | 1.2% |
| Aloe Vera (1:100) | 2% |
| Witch Hazel extract | 4% |
| Sulfur (MSM) | 4% |
| Vitamin C (Ascorbic acid) | 0.01% |
| Vitamin B12 (Methylcobalamin) | 0.01% |
| Vitamin E (Tocopherol) | 0.092% |
| Omega 3,6,7,9 | 0.08% |
| Menthol oil | 0.008% |

Table 7 discloses a non-limiting formulation that may be used as a formulation for softening, moisturizing and lubricating formulation.

TABLE 7 formulation for softening, moisturizing and lubricating formulation.

| Compound | Percentage by weight |
|---|---|
| Purified water: preferably purified or distilled | 49% |
| Magnesium Chloride | 15% |
| Calcium Oxide | 1.7% |
| Potassium Phosphate | 0.05% |
| Sodium Carbonate | 0.5% |
| Salts:(Dead Sea salts 3.2%, Sea salt 0.5%, Himalayan salt 0.3%) | 4% |
| Zinc Citrate | 0.8% |
| Jojoba oil | 6% |
| Grape seed oil | 3% |
| Rose hip oil | 0.1% |
| Silica dioxide spheres 5-15 micron | 2.5% |
| Apple cider vinegar | 3% |
| Emulsifiers combination (Agar 0.3%, Xanthan gum 0.4%, Acacia 0.122 | 0.822% |
| Aloe Vera juice concentrate (1:100/1:200) | 4% |
| Witch Hazel extract | 4.5% |
| Sulfur (MSM) | 4% |
| Vitamin C (Ascorbic acid) | 0.01% |
| Vitamin B12 (Methylcobalamin) | 0.01% |
| Vitamin E (Tocopherol) | 0.5% |
| Omega 3,6,7,9 | 0.5% |
| Menthol oil | 0.008% |

All formulas are prepared by using standard mixing methods commonly practice by those skilled in the art. The formulations may also be sprayed or mixed into a gel, cream, or paste, by the addition of thickeners, including but not limited to Guar gum, *Psyllium*, and Xanthan gum.

In the current skin care market, there are many cosmetic products such as deodorants, skin lotions for hydrating, calming, soothing, moisturizing and lubricating which contain ingredients recently linked to serious diseases such as cancer and Alzheimer, as well as ingredients which cause skin irritations after prolonged use. The disclosed invention uses only ingredients which are known to be safe and ingredients which are generally recognized as safe (GRAS) and does not contain ingredients reported to be irritating or toxic including but not limited to aluminum compounds, polypropylene glycol, baking soda, alcohol, parabens, Phthalates, Triciosan, or petroleum based ingredients.

Non-limiting examples of uses or applications for the formulations of the invention, include skin hydration, softening, soothing, reduce redness and swelling, restore acidic pH level, calming, cooling sensation, warming sensation, anti-bacterial effect, deodorizing, detoxifying, clearing pores, shrinking pore size, whitening/brightening of the skin, remineralizing, support for hair growth, as well as anti-chafing barrier. The Inventors have made the surprising discovery that the various formulations of the invention will help the skin to return to normal from many damaged states including but not limited to: rashes, fever blisters, cold sores, nail fungus, athlete's foot, acne, pimples, as well as dark areas and skin spots. In addition, either the core formula or the any the various formulations may provide a carrier for cosmetics, fragrances, or therapeutic products.

Preferred embodiments of the invention are described in the following non-limiting examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims.

What is claimed is:

1. An aqueous skin care formulation, comprising:
   a) a combination of minerals, comprising:
      i. magnesium compounds, about 0.001% to about 20%;
      ii. calcium compounds, about 0.002% to about 9%; and
      iii. potassium compounds, about 0.001% to about 6%;
   b) one or more of Jojoba oil, about 0.005% to about 6%; Grape Seed Oil, about 0.005% to about 6%; or Rose Hip Oil, about 0.005% to about 6%;
   c) one or more of AgarAgar, about 0.005% to about 0.4%; Xanthan gum, about 0.005% to about 0.4%; Acacia, about 0.005% to about 0.4%; and
   d) sufficient water to comprise 100%; and
   e) wherein the skin care formulation does not comprise an irritating or toxic compound selected from the group consisting of: Propylene Glycol, Butylene Glycol, Sodium bicarbonate, Benzoyl peroxide, DEA/TEA/MEA, Ethoxylated surfactants and 1,4-dioxane, Formaldehyde, Synthetic Fragrance, Mineral oils, petroleum, Oxybenzone, Parabens, Phthalates, Polyethylene glycol, Silicone-derived emollients, Sodium lauryN (ether) suNfate, Talc, TricNosan, Potassium Alum, Ammonium Alum, butylated hydroxyanisole (BHA), Boric acid and Sodium borate.

2. The composition of claim 1, further comprising natural oils selected from the group consisting of: Almond oil, Aloe Vera oil, Apricot kernel oil, Avocado oil, Calendula oil, Coconut oil, Evening primrose oil, Grape seed oil, Hazelnut oil, Jojoba oil, Macadamia oil, Rosehip oil, Sesame oil, Walnut oil, Wheat germ oil, Olive oil, Pumpkin seed oil, Safflower oil, Sunflower oil, cocoa butter, and palm oil.

3. The composition of claim 1, further comprising emulsifiers selected from the group consisting of Acacia gum, Algae, Xanthan gum, Cellulose compounds, Lecithin, Guar gum, Agar agar, Pectin fruit, Gellan gum, Locust bean gum, and *Psyllium*.

4. The composition of claim 1, further comprising:
   a) guar gum, *psyllium*, or Methyl cellulose, from about 0.8% to about 4%; and
   b) Arrow root powder, from about 5% to about 10%; and
   c) wherein the formulation is mixed to a cream or paste.

5. The composition of claim 1, further comprising:
a) coconut oil, from about 2.5% to about 5%;
b) a natural wax, from about 10% to about 20%;
c) cocoa butter or palm oil from about 8% to about 15%;
d) wherein the formulation is mixed to a balm.

6. The composition of claim 1, further comprising Beef tallow, from about 5% to about 25%, wherein the formulation may be mixed to a mineral rich skin softening lotion.

7. The composition of claim 1, further comprising:
a) Beef tallow from about 5% to about 25%;
b) A natural wax from about 10% to about 20%;
c) cocoa butter, or palm oil from about 8 percent to 15%; and
d) wherein the formulation is mixed to a skin balm.

8. An aqueous skin care deodorant formulation, comprising:
a) Water, about 46 percent;
b) Magnesium Glycinate, about 10 percent;
c) Calcium Carbonate, about 3 percent
d) Potassium Chloride, about 1 percent
e) Sodium Carbonate, about 1.7 percent;
f) Dead Sea salts, about 7.5%, percent;
g) Sea salt, about 0.5%, percent;
h) Himalayan salt, about 0.3% percent;
i) Zinc oxide, about 2.3 percent;
j) Jojoba oil, about 2.5 percent;
k) Grape seed oil, about 1.7 percent;
l) Rose hip oil, about 1.2 percent;
m) Silica dioxide spheres 5-15 micron, about 9.4 percent;
n) Apple cider vinegar, about 1.5 percent;
o) Agar agar about, 0.4%, percent;
p) Xanthan gum, about 0.4%, percent;
q) Acacia gum, about 0.4 percent;
r) Aloe Vera juice concentrate (1:100/1:200), about 2 percent;
s) Witch Hazel extract, about 4 percent;
t) Sulfur (MSM), about 4 percent;
u) Vitamin C, about 0.01 percent;
v) Vitamin B12, about 0.01 percent;
w) Vitamin E, about 0.092 percent;
x) One or more omega 3, 6, 7, 9 oil, about 0.08 percent; and
y) Menthol oil about 0.008 percent; and
z) wherein the aqueous skin care deodorant formulation does not comprise an irritating or toxic compound selected from the group consisting of: Propylene Glycol, Butylene Glycol, Sodium bicarbonate, Benzoyl peroxide, DEA/TEA/MEA, Ethoxylated surfactants and 1,4-dioxane, Formaldehyde, Synthetic Fragrance, Mineral oils, petroleum, Oxybenzone, Parabens, Phthalates, Polyethylene glycol, Silicone-derived emollients, Sodium lauryN (ether) suNfate, Talc, TricNosan, Potassium Alum, Ammonium Alum, butylated hydroxyanisole (BHA), Boric acid and Sodium borate.

9. An aqueous skin care formulation for softening, moisturizing and lubricating skin, comprising:
a) Water, about 49 percent;
b) Magnesium Chloride, about 15 percent;
c) Calcium Oxide about 1.7 percent
d) Potassium Phosphate about 1 percent
e) Sodium Carbonate, about 0.05 percent;
f) Dead Sea salts, about 3.2, percent;
g) Sea salt, about 0.5, percent;
h) Himalayan salt, about 0.3 percent
i) Zinc Citrate, about 0.8 percent;
j) Jojoba oil, about 2.5 percent;
k) Grape seed oil, about 3 percent;
l) Rose hip oil, about 0.1 percent;
m) Silica dioxide spheres 5-15 micron, about 2.5 percent;
n) Apple cider vinegar, about 3 percent;
o) Agar about, 0.3%, percent;
p) Xanthan gum, about 0.4, percent;
q) Acacia, about 0.122 percent;
r) Aloe Vera juice concentrate (1:100/1:200), about 4 percent;
s) Witch Hazel extract, about 4.5 percent;
t) Sulfur (MSM), about 4 percent;
u) Vitamin C, about 0.01 percent;
v) Vitamin B12, about 0.01 percent;
w) Vitamin E, about 0.5 percent;
x) One or more omega 3, 6, 7, 9 oil, about 0.5 percent; and
y) Menthol oil about 0.008 percent; and
z) wherein the aqueous skin care deodorant formulation does not comprise an irritating or toxic compound selected from the group consisting of: Propylene Glycol, Butylene Glycol, Sodium bicarbonate, Benzoyl peroxide, DEA/TEA/MEA, Ethoxylated surfactants and 1,4-dioxane, Formaldehyde, Synthetic Fragrance, Mineral oils, petroleum, Oxybenzone, Parabens, Phthalates, Polyethylene glycol, Silicone-derived emollients, Sodium lauryN (ether) suNfate, Talc, TricNosan, Potassium Alum, Ammonium Alum, butylated hydroxyanisole (BHA), Boric acid and Sodium borate.

10. A method of treating dry skin, comprising, applying the skin care formulation of claim 1, to the skin.

11. A method of treating dry skin, comprising, applying the skin care formulation of claim 4, to the skin.

12. A method of treating dry skin, comprising, applying the skin care formulation of claim 5, to the skin.

13. A method of softening the skin comprising, applying the skin care formulation of claim 6, to the skin.

14. A method of softening the skin comprising, applying the skin care formulation of claim 7, to the skin.

15. A method of deodorizing skin, comprising, applying the skin care deodorant formulation of claim 8, to the skin.

16. A method of softening, moisturizing and lubricating skin, comprising, applying the skin care formulation of claim 9, to the skin.

* * * * *